(12) United States Patent
Hunt et al.

(10) Patent No.: US 7,585,681 B2
(45) Date of Patent: Sep. 8, 2009

(54) METHOD FOR EVALUATING BINDER DISTRIBUTION ON A SURFACE

(75) Inventors: Robert N. Hunt, Steubenville, OH (US); Theodore S. Frick, Moon Township, PA (US)

(73) Assignee: Bayer MaterialScience LLC, Pittsburgh, PA (US)

( * ) Notice: Subject to any disclaimer, the term of this patent is extended or adjusted under 35 U.S.C. 154(b) by 983 days.

(21) Appl. No.: 10/677,187

(22) Filed: Oct. 2, 2003

(65) Prior Publication Data

US 2005/0079632 A1  Apr. 14, 2005

(51) Int. Cl.
*G01N 21/76* (2006.01)
*G01N 1/18* (2006.01)
*B32B 5/12* (2006.01)
*B05D 3/12* (2006.01)
*B05D 3/02* (2006.01)

(52) U.S. Cl. .............. 436/172; 436/177; 436/178; 428/113; 428/106; 427/351; 427/393

(58) Field of Classification Search ............. 436/172, 436/177, 178; 428/113, 106; 427/351, 393
See application file for complete search history.

(56) References Cited

U.S. PATENT DOCUMENTS

| | | | |
|---|---|---|---|
| 4,651,011 A | 3/1987 | Ors et al. ............ 250/459.1 |
| 4,885,254 A | 12/1989 | Sung .................... 436/85 |
| 4,922,113 A | 5/1990 | Melancon ............. 250/372 |
| 5,100,802 A | 3/1992 | Mickols ................ 436/34 |
| 5,455,217 A * | 10/1995 | Chang et al. .......... 503/227 |
| 6,867,421 B1 * | 3/2005 | Hunt et al. ........... 250/461.1 |

OTHER PUBLICATIONS

Saito et al., Direct Evidence for Low-Density Regions in Compacted Spray-Dried Powders, J. Am. Ceram. Soc. vol. 84, No. 10, pp. 2454-2456, 2001.*
Institute of Materials Science, Storrs Report TR-38-0NR, Connecticut University, Jun. 1, 1994, Sun et al,"Intrinsic Fluorescence Cure Sensor for Reaction Monitoring in Polyurethane".
Forest Products Society, vol. 46, No. 6, Jun. 1996, pp. 63-68, F.A. Kamke et al, "Measurement Of Resin and Wax Distribution on Wood Flakes", F. Kamke's work in reported Wood Base Composites Program Annual Report (Jun. 1, 1994-May 31, 1995).

* cited by examiner

*Primary Examiner*—Vickie Kim
*Assistant Examiner*—Keri A Moss
(74) *Attorney, Agent, or Firm*—Lyndanne M. Whalen

(57) ABSTRACT

A method and apparatus for determining binder distribution on a sample in which a selected sample is contacted with a transfer medium in a manner such that at least 15% of any fluorescing binder present on the surface of the sample will be transferred to the transfer medium, a digital image of the transfer medium is generated and analyzed for binder distribution.

9 Claims, 5 Drawing Sheets

METHOD FOR EVALUATING BINDER DISTRIBUTION ON A SURFACE

BACKGROUND OF THE INVENTION

The present invention relates to a method for evaluating binder distribution on a surface such as wood particles or strands.

Various types of binders have been used to produce engineered composite materials such as oriented strand board. Suitable binders include phenol formaldehyde resins and isocyanates, particularly polymeric diphenylmethane diisocyanate ("PMDI"). In producing such engineered composites, the binder is generally applied to a material such as wood fibers, wood strands, wood flakes or some other lignocellulose-based material. Ideally, the amount of binder applied ("dosage") would be sufficient to cover 100% of the surface of 100% of the wood fibers, wood strands, etc. ("distribution"). In most commercial processes, an excess of binder is used to ensure sufficient distribution. Longer than necessary mixing times may also be used to ensure that the binder is sufficiently distributed so that weak spots in the composite material due to insufficient adhesion do not occur. This use of excess binder and extended mixing times significantly increases the cost of producing engineered composite materials.

It would therefore be advantageous to develop a method for determining binder distribution during the composite production process with sufficient accuracy that use of excess binder and extended mixing times are unnecessary.

spectroscopic methods for making such determinations have been investigated by those seeking to improve the production of composite materials. Solid NMR characterization of the bonding of composite materials was studied by Frazier and Wendler and the results were presented in "15N CP/MAS NMR analysis of pMDI bonded cellulose composites" presented at the 48th Annual Meeting of the Forest Products Society, Portland, Me., Jun. 26-29, 1994. Sun et al attempted to correlate fluorescence intensity changes with FTIR spectra generated by monitoring the disappearance of the isocyanate group during the reaction which occurs in the commercial production process. (See, e.g., Sun et al, Institute of Materials Science, Storrs Report TR-38-ONR, Connecticut University (1994).)

UV absorption and fluorescence spectroscopy are also techniques which have been evaluated for their usefulness in monitoring urethane-forming reactions. However, many of these spectroscopic techniques are not capable of providing timely analysis of binder distribution, particularly when the particulate material being bonded is very light or dark in color.

For example, F. Kamke's work reported in "Wood Based Composites Program Annual Report" (Jun. 1, 1994-May 31, 1995) was a microscopic study of UV fluorescence imaging of polymeric MDI resin distribution on wood strands. Kamke states that because polymeric MDI fluorescence is very weak, a very intense UV source (specifically, a 100 watt mercury vapor lamp) and signal averaging of many video frames to reduce noise level were necessary. Microscopic evaluation of a material is impractical for monitoring a commercial production process because of the great potential for variation between samples.

Yu et al report a technique in which naphthylene diisocyanate is used as a molecular sensor to monitor cure reactions in a polyurethane in U.S. Pat. No. 4,885,254. Yu et al correlate the fluorescence intensity and overall extent of reaction between 1,5-naphthyl diisocyanate and n-butanol. This correlation was established by identifying the various species present during the urethane-forming reaction using HPLC that was confirmed by IR spectra. The UV-visible absorption spectrum and fluorescence spectrum for each of these species were then generated. Shifts in the UV-visible spectrum were observed as the naphthyl diisocyanate reacted to form the monourethane and diurethane. The fraction of each species present at a given time was determined by linear regression analysis. The extent of the reaction was calculated from UV spectral analysis. A correlation between the experimentally determined fluorescence intensity at 357 nanometers and the calculated overall extent of reaction derived from UV spectral analysis was made.

U.S. Pat. No. 5,100,802 discloses a method for measuring the rate and extent of cure of a resin system in which a fluorescent dye is added to the system being polymerized.

U.S. Pat. No. 4,922,113 discloses a method for monitoring a coating's weight, uniformity and surface defects in which a UV-escer that absorbs radiant energy is included in the coating composition. The radiant energy emitted by the coating at the same wavelength as energy emitted by the UV-escer can be detected and correlated to pre-established standards.

U.S. Pat. No. 4,651,011 discloses a method for determining the extent of cure of a polymer. In this method, the degree of free space rotation of a fluorospore added to the polymer system is determined by fluorescent measurement of the fluorospore.

However, no method for reliably determining binder distribution on particles or strands which are either very light or dark in color during actual production of composite materials without the addition of some type of "marker" such as a dye, fluorospore or UV-escer has been developed.

SUMMARY OF THE INVENTION

It is an object of the present invention to provide a method for determining binder distribution on a sample or samples selected from a composite-forming composition such as wood particles or strands (particularly samples which are dark or very light in color) during the production of a composite material.

It is also an object of the present invention to provide a method for accurately determining binder distribution during production of a composite from a composite-forming material that is light or dark in color without using a marker material such as a UV-escer, fluorospore or dye.

These and other objects of the present invention which will be apparent to those skilled in the art are accomplished by (1) selecting one or more samples (e.g., strand(s) or particle(s)) to be evaluated, (2) contacting the sample with a transfer medium in a manner such that at least 15%, preferably at least 25% of any binder present on the sample surface is transferred to that transfer medium, (3) generating a digital image of the transfer medium which had been in contact with the sample, (4) analyzing any spots present in the image of the transfer medium for size and area, and (5) correlating these measurements with a binder distribution standard.

DETAILED DESCRIPTION OF THE PRESENT INVENTION

Figure 1:
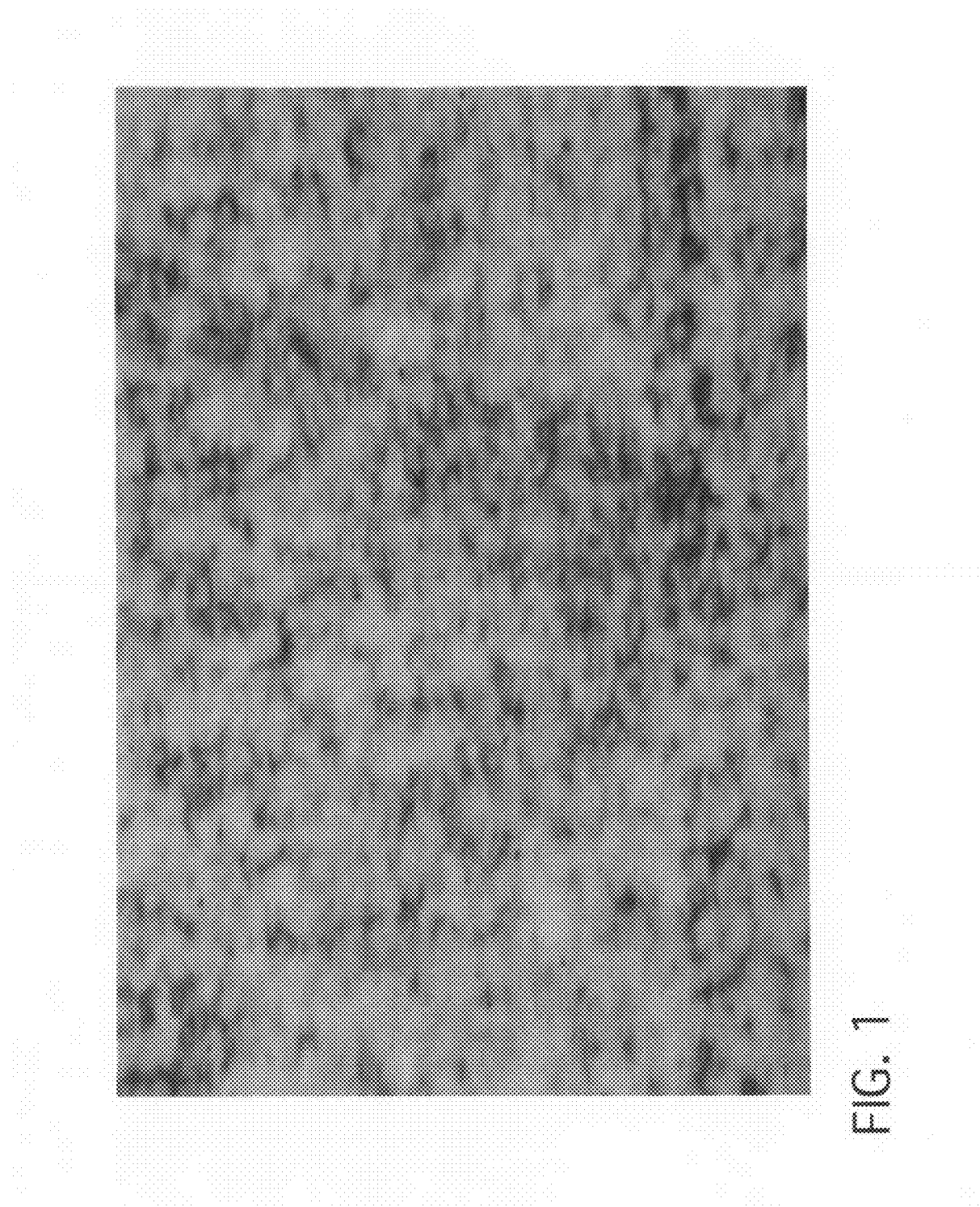
FIG. 1 is a resin print of a transfer medium for a wood strand selected from a composite-forming mixture to which 5% resin binder had been applied. This wood strand was 92% covered with binder and had binder spots with diameters averaging 0.711 mm.

The present invention is directed to a method for determining binder distribution on the particles or strands from which composite materials are to be produced without the need to add a UV-escer, fluorospore or dye solely for the purpose of determining binder distribution.

The method of the present invention is particularly useful where the color of the sample material is sufficiently light or dark in color to interfere with the ability to analyze it spectrographically.

In the method of the present invention, the sample particles or strands selected from the composite-forming mixture are contacted with a transfer medium in a manner such that at least 15%, most preferably at least 25% of any binder present on the selected particle or strand will be transferred to that transfer medium. A digital image of this transfer medium is then generated and analyzed.

As used herein, the expression "sample" includes one or more strands, fibers, filaments, particles or shavings of a material being used to produce a composite article such as oriented strand board, particleboard or medium density fiberboard.

The composite-forming material may be made up of any of the materials, particularly lignocellulosic materials, known to be useful for the production of composite materials using a binder, preferably an isocyanate-based binder. Examples of suitable composite-forming materials include: wood, wood fibers, wood bark, cork, wheat straw, rice straw, bagasse straw, rye grass, flax, bamboo, esparto, rice hulls, sunflower hulls, sisal fibers and coconut fibers. Wood strands, shavings and chips used in the production of engineered lumber known as oriented strand board ("OSB") are particularly preferred. The strands, chips or shavings may vary in size from 0.03"×0.18"×2.0" to 0.12"×2.0"×28.0". The preferred size ranges from 0.03"×1.0"×16" to 0.12"×2.0"×24" and the most preferred range is from 0.03"×0.75"×3.0" to 0.12"×2.0"×24". These lignocellulosic materials may have a moisture content of from about 0.5 to about 30% by weight, based on total weight of lignocellulosic material, preferably from about 1.5 to about 8% by weight when used in the production of a composite material.

The distribution of any binder composition having a fluorescing component may be determined by using the method of the present invention. Such binder compositions are known to those skilled in the art and include materials such as isocyanates. The preferred binder compositions are polyphenylene polymethylene polyisocyanates ("polymeric MDI") which contain higher molecular weight oligomers (i.e., oligomers having more than four rings) that have an inherent fluorescence and thus do not require the addition of a fluorescing agent to the binder composition. The binder should preferably have a minimum of 20%, preferably at least 25% by weight of oligomers with more than four aromatic rings.

The transfer medium contacted with the sample to be evaluated may be any medium which is absorptive, non-wicking and does not contain any dyes or whiteners. The transfer medium must be capable of absorbing the binder from the sample in a manner such that the binder does not spread on that transfer medium. Filter paper, particularly, medium fine to fine grades of filter paper, is an example of a suitable transfer medium. Filter paper has the advantage of being readily available in most testing facilities. Specific examples of filter papers which have been found to be useful in the practice of the present invention are Fisher brand Filter Paper Grade P2 (Fisher Scientific) and Whatman Qualitative Filter Paper Grades Whatman 2, 3, 5 and 6 (Fisher Scientific).

In the method of the present invention, the sample material may be placed between two sheets of the transfer medium (e.g., filter paper) or the transfer medium may be folded in a manner such that essentially the total surface of the sample is in physical contact with that medium. Sufficient pressure or force is applied to the transfer medium between which the sample has been placed for a sufficient amount of time to ensure that at least 15% of any binder present on the surface of the sample will be transferred to that transfer medium.

Adequate transfer of the binder is assured by subjecting each sample to the same degree of a pre-determined pressure for the same pre-determined period of time. The appropriate amount of pressure and time may be established by a simple preliminary procedure. For example strands of the wood and the transfer medium to be used may be weighted, a known amount of binder applied, the resin-coated wood strands subjected to a selected amount of pressure for a selected amount of time, weighing the transfer medium to which the binder has been transferred determining the weight of binder transferred to the transfer medium and calculating the percentage of total binder transferred from the sample to the transfer medium. This procedure is repeated until an appropriate pressure and time period to ensure adequate binder transfer are determined. Once established, the sample size, amount of pressure applied and the time the sample remains under that pressure should remain relatively consistent.

The sample is then removed from the transfer medium. A digital image of the binder on the transfer medium may then be generated by making the binder fluoresce by exposing it to ultraviolet radiation, preferably long wave ultraviolet radiation (i.e., wavelengths of from 3200 to 4000 Angstroms) and then taking a picture of the fluorescing binder with a high resolution digital camera. A suitable digital image may also be generated by taking a picture of the binder on the transfer medium with a standard, film camera and then scanning the resultant photograph to produce a digital image. An electronic line scan camera will also generate a suitable digital image. Use of a digital camera with a minimum 2.1 megapixel CCD imaging sensor that is capable of generating a picture with a resolution of 1792×1200 is particularly preferred.

The digital image is then analyzed using any program capable of determining the spot size and area of coverage of the fluorescing binder from such an image. Suitable, commercially available programs useful for performing this analysis include: Wit Visual Programming Software (Logical Vision, a Division of Coreco, Inc.); Image-Pro Plus (Media Cybernetics, Inc.) Visilog Pro™ Image Processing Software (Edmond Optics, Inc.) and ImageJ Java-based public domain software. The Wit Visual Programming Software has been found to be particularly useful.

The data generated by such analysis of a number of randomly selected samples may then be compared to standards which have been established by evaluating coated samples with a known degree of coverage and known amount of material in accordance with the method of the present invention.

The determined binder distribution characteristics may then be displayed on a monitor, printed or converted to an analog signal for output to other instrumentation. The results may be in the form of an image of the sample in the actual fluorescing color or a false color image with a palette reflecting binder distribution.

Any of the commercially available computers or data processors may be used as image processing hardware in the practice of the present invention. Computers which have been found to be particularly advantageous are those having a 233 MHz or faster Intel Pentium Processor Any of the commercially available image processing software programs that can be installed on computer hardware may be used in the apparatus of the present invention. One software program that has been found to be particularly advantageous in the practice of the present invention is the Wit Visual Programming Software that is available from Logical Vision, Quebec, Canada.

Any of the commercially available monitors may be used in the practice of the present invention as monitor. It is preferred, however, that any monitor employed be capable of displaying images and/or spectra in color.

The composite-forming material from which sample(s) are selected may be prepared by mixing or blending a lignocellulose-based material with the binder. Samples are selected either before or after the composite-forming mixture or blend is deposited into a mold or a form or on a conveyor belt, but before the composite-forming material is passed through a heated press to cure the binder composition.

The distribution of binder is then determined in accordance with the method of the present invention at a location removed from the curing oven such as a process control room or a quality control lab. The results of such analysis make it possible to optimize the production process and achieve significant savings due to the use of less binder.

Having thus described our invention, the following Examples are given as being illustrative thereof. All parts and percentages given in these Examples are parts by weight and percentages by weight, unless otherwise indicated.

EXAMPLES

Example 1

Figure 2:
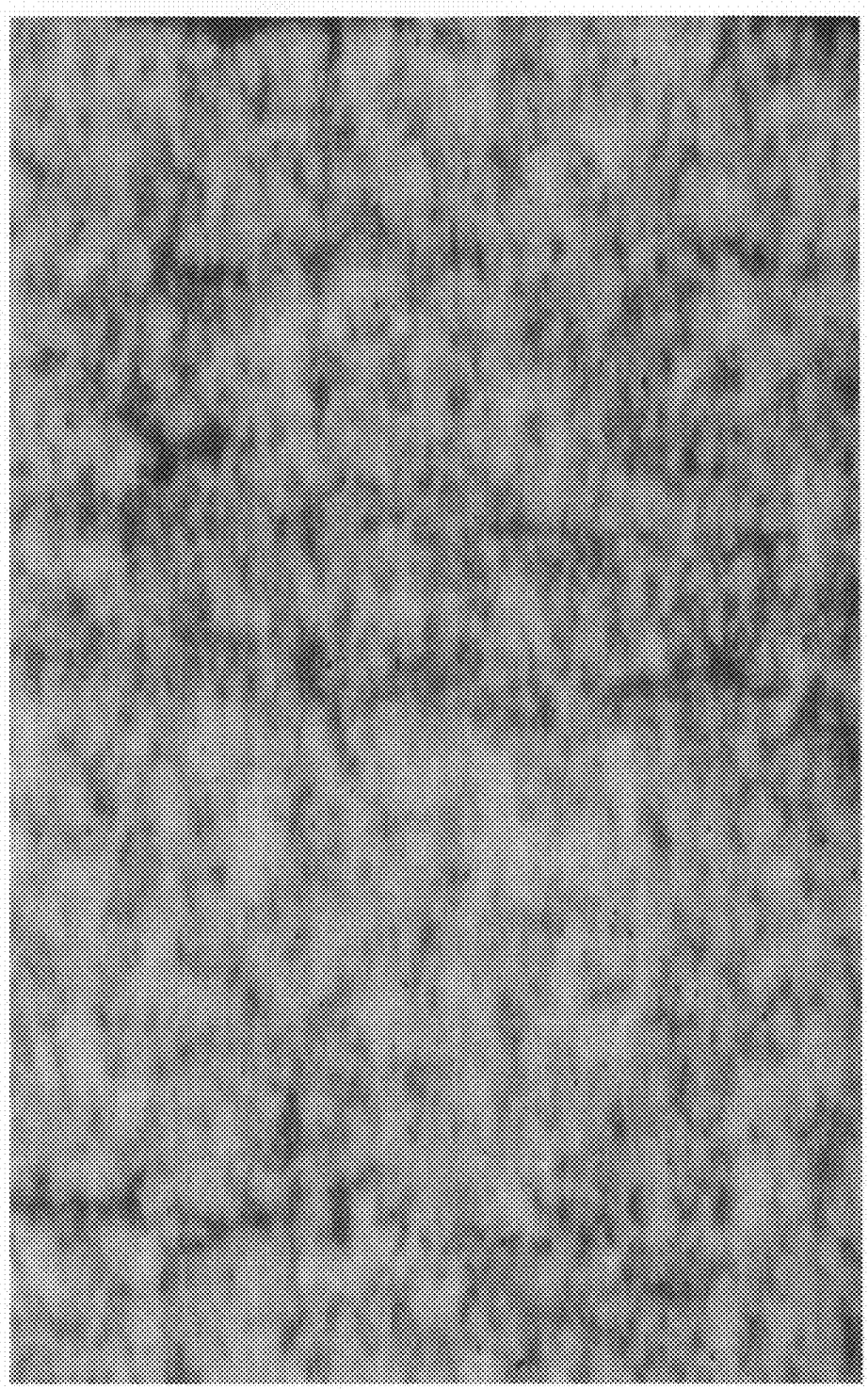
FIG. 2 is a resin print of a transfer medium for a wood strand selected from a composite-forming mixture to which 5% resin binder had been applied. This wood strand was 76% covered with binder and had binder spots with diameters averaging 0.340 mm.

5 kg of wood furnish (southern yellow pine) were added to a laboratory drum blender and blended with 5 wt %, based on the weight of the dry wood furnish, of polymeric MDI which is commercially available from Bayer Polymers LLC under the name Mondur 541 Light using a spinning disk atomizer. Strands of the coated wood were pressed between pieces of white filter paper (Whatman Qualitative Filter Paper, grade Whatman 2) for 30 seconds using a rubber-padded vice tightened with a torque wrench to 15 to 20 ft-lb. After the wood was removed from the filter paper, a picture of the filter paper was taken while being exposed to UV radiation from a General Electric FC8T9-BLB black light using a Kodak model DC290 digital camera. The image thus generated was then analyzed using Wit Visual Programming software. FIGS. 1 and 2 show the images obtained. Analysis of these images indicated resin coverage of 92% (FIG. 1) and 76% (FIG. 2) and average spot diameters of 0.711 mm (FIG. 1) and 0.340 mm (FIG. 2).

Example 2

Figure 3:
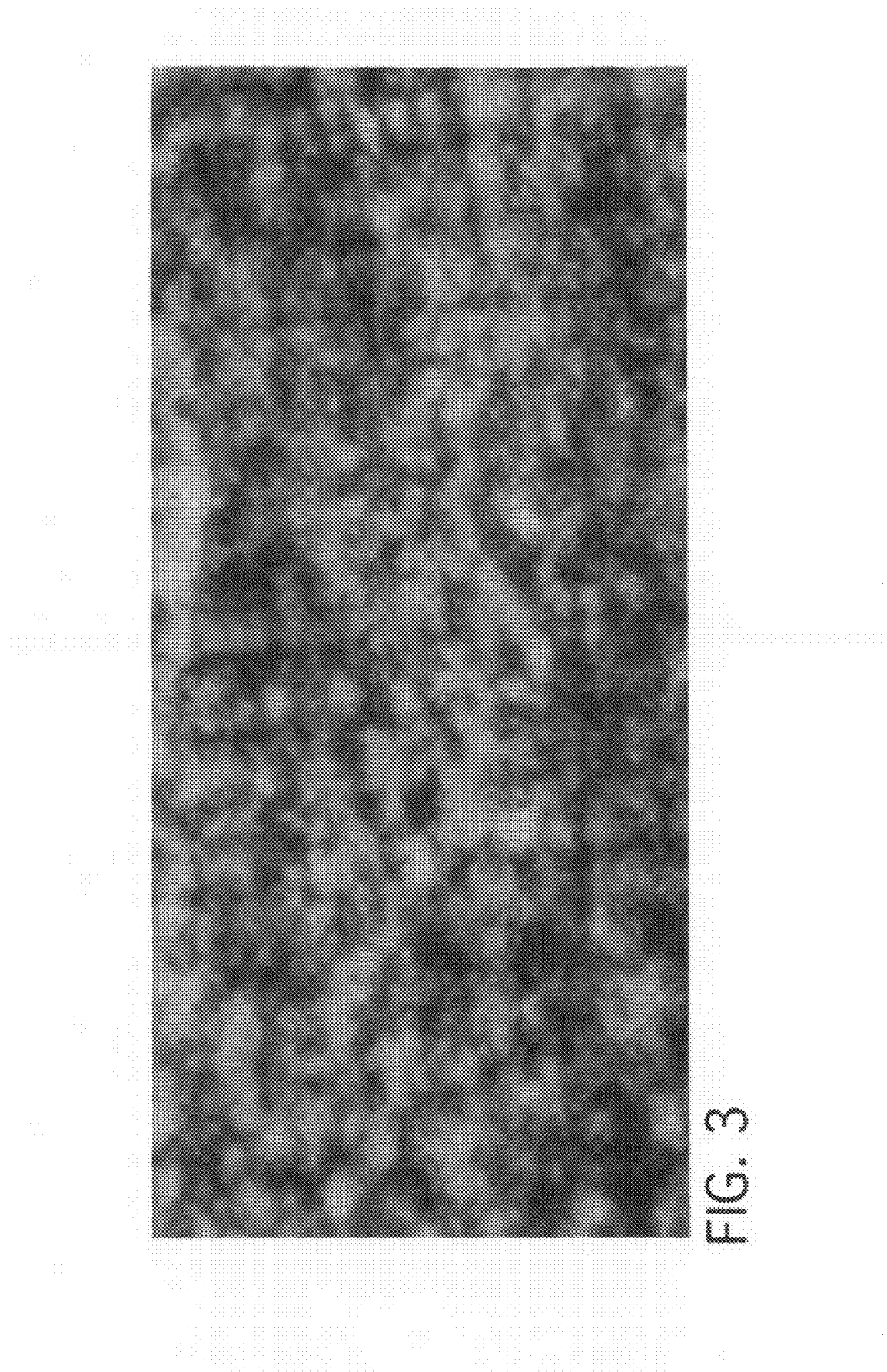
FIG. 3 is a resin print of a transfer medium for a wood strand selected from a composite-forming mixture to which 3.5% resin binder had been applied. This wood strand was 22% covered with binder and had binder spots with diameters averaging 0.171 mm.

The procedure of Example 1 was repeated with the exception that the amount of polymeric MDI used was 3.5 wt %, based on the weight of the wood furnish. FIG. 3 shows the image obtained. Analysis of this image using the Wit Visual Programming Software indicated a resin coverage of 22% and an average spot diameter of 0.171 mm.

Example 3

Figure 4:
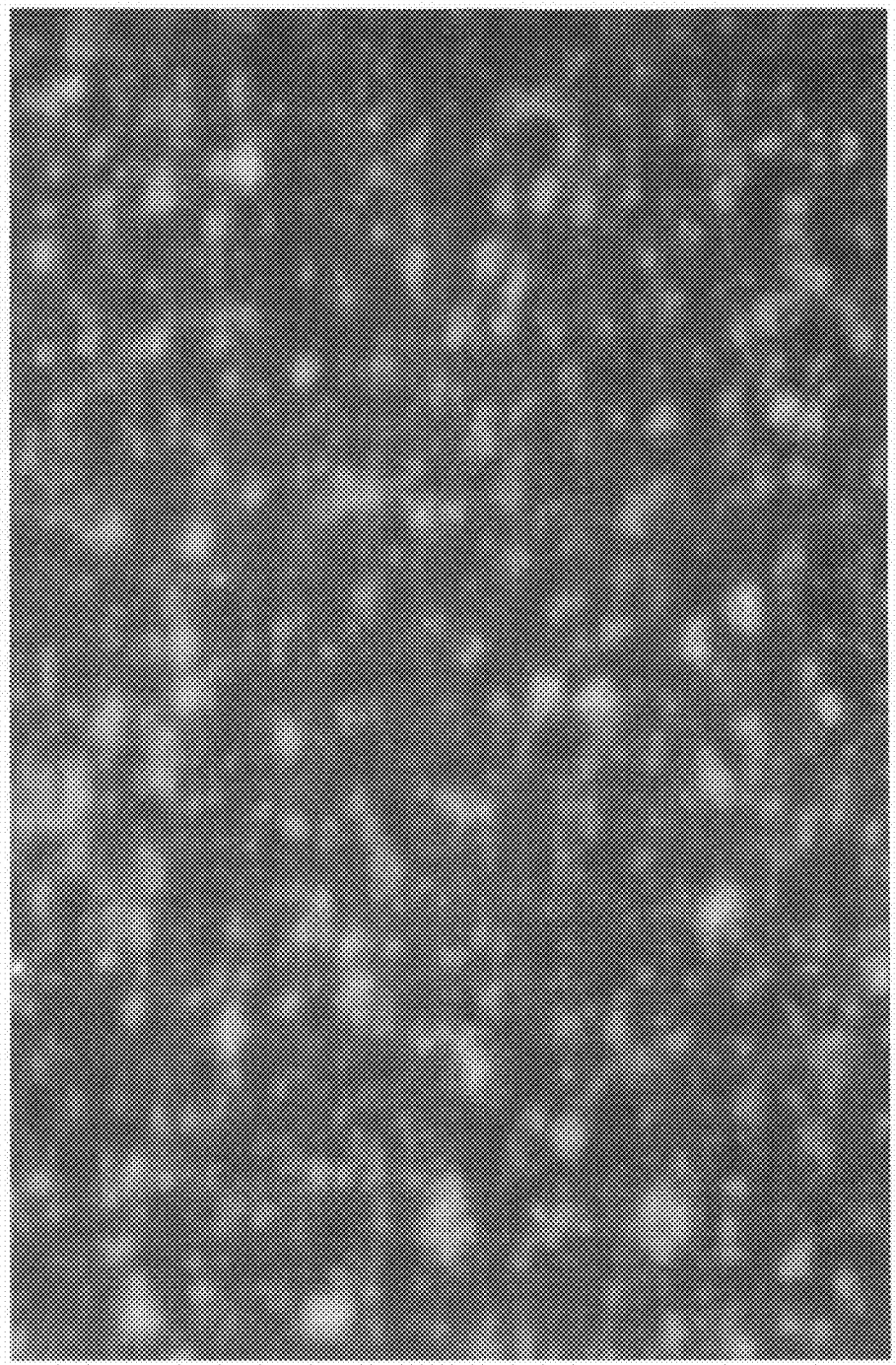
FIG. 4 is a resin print of a transfer medium for a wood strand selected from a composite-forming mixture to which 2% resin binder had been applied. This wood strand was 3% covered with binder and had binder spots with diameters averaging 0.118 mm.
Figure 5:
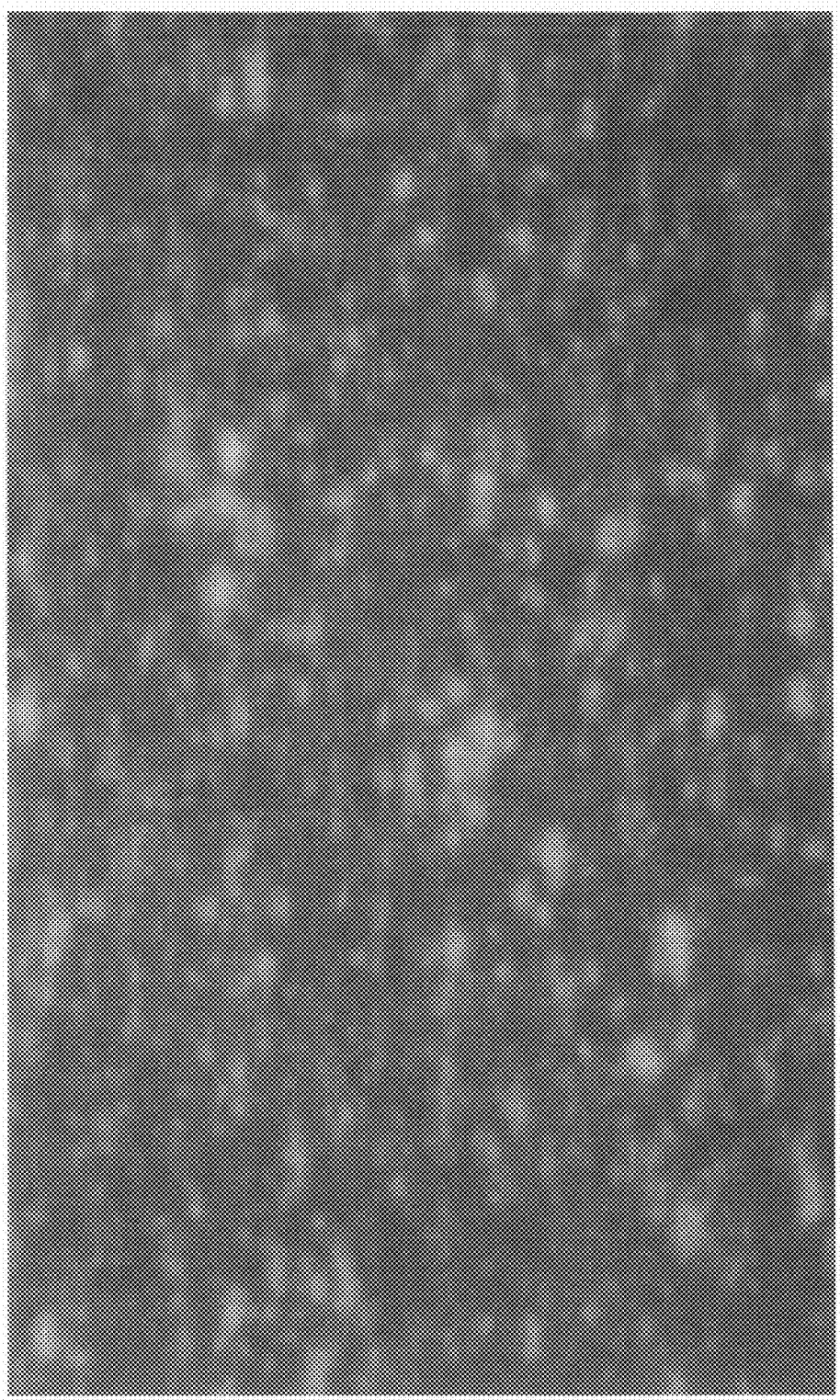
FIG. 5 is a resin print of a transfer medium for a wood strand selected from a composite-forming mixture to which 2% resin binder had been applied. This wood strand was 1% covered with binder and had binder spots with diameters averaging 0.096 mm.

The procedure of Example 1 was repeated with the exception that the amount of polymeric MDI used was 2.0 wt %, based on the weight of the wood furnish. FIGS. 4 and 5 show the images obtained. Analysis of these images indicates a resin coverage of 3% (FIG. 4) and 1% (FIG. 5) and average spot diameters of 0.118 mm (FIG. 4) and 0.096 mm (FIG. 5).

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A method for determining binder distribution on a sample comprising:
   a) selecting a sample,
   b) contacting the sample with filter paper in a manner such that at least 15% of any isocyanate binder present on the sample surface is transferred to the filter paper,
   c) exposing the filter paper from b) to ultraviolet radiation to make the isocyanate binder fluoresce,
   d) imaging visible wave emissions of the fluorescing isocyanate binder present on the filter paper onto a camera,
   e) converting the image generated in d) to an electronic signal, and
   f) relaying the electronic signal generated in e) to a means for correlating distribution of isocyanate binder to the electronic signal received.

2. The method of claim 1 in which at least 25% of any binder present on the sample is transferred to the transfer medium in step b).

3. The method of claim 1 in which the binder is polymeric MDI.

4. The method of claim 1 in which the binder is a polyisocyanate-based material having an oligomeric content of at least 20%.

5. The method of claim 1 in which the binder is a polyisocyanate-based material having an oligomeric content of at least 25%.

6. The method of claim 1 in which the means for correlating distribution of binder to the electronic signal received in step e) is a computer.

7. The method of claim 1 in which the camera used to image the visible wave emissions is also capable of converting the image to an electronic signal.

8. The method of claim 1 in which the transfer medium is exposed to long wave ultraviolet radiation in step c).

9. A process for the production of wood strand board comprising
- a) applying a polyisocyanate to wood strands,
- b) monitoring the polyisocyanate/wood strand material in accordance with the method of claim 1 until the polyisocyanate distribution is within a previously determined acceptable range,
- c) forming the polyisocyanate/wood strand material into the desired shape or form, and
- d) subjecting the polyisocyanate/wood strand material to curing conditions.

* * * * *